US00PP34136P2

(12) United States Plant Patent
Legarra

(10) Patent No.: US PP34,136 P2
(45) Date of Patent: Apr. 19, 2022

(54) CLEMENTINE MANDARIN TREE NAMED 'AECO1'

(50) Latin Name: ***Citrus* x *clementina***
Varietal Denomination: AECO1

(71) Applicant: Gestion Ecosistemas Agricolas S.L., Valencia (ES)

(72) Inventor: Estanislao Garavilla Legarra, Valencia (ES)

(73) Assignee: Gestion Ecosistemas Agricolas S.L.

( * ) Notice: Subject to any disclaimer, the term of this patent is extended or adjusted under 35 U.S.C. 154(b) by 0 days.

(21) Appl. No.: 17/307,198

(22) Filed: May 4, 2021

(51) Int. Cl.
*A01H 5/08* (2018.01)
*A01H 6/78* (2018.01)

(52) U.S. Cl.
USPC ..... Plt./202

(58) Field of Classification Search
USPC ..... Plt./202, 201
CPC ... A01H 5/08; A01H 5/00; A01H 6/78; A01H 6/785; A01H 6/00; A01H 6/74
See application file for complete search history.

(56) References Cited

PUBLICATIONS

Boletin del Registro de Variedades Cimerciales Boletin No. 6/2019, retireved on Aug. 4, 2021, retrieved from the Internet at https://www.mapa.gob.es/ministerio/pags/Biblioteca/Revistas/pdf_RVC%2FBOL-RVC-6-2019.pdf, pp. 1-3,5. (Year: 2019).*

* cited by examiner

*Primary Examiner* — June Hwu
(74) *Attorney, Agent, or Firm* — Cassandra Bright

(57) ABSTRACT

A new distinctive clementine mandarin tree variety named 'AECO1' particularly characterized by abiotic stress resistance, early harvest period, high productivity, a flattened fruit shape and the bright intense orange skin color. The fruit shows a significant holding post maturity ability on tree for nearly 3 months (no puffing).

4 Drawing Sheets

Latin name of the genus and species: *Citrus* x *clementina*.
Variety denomination: 'AECO1'.

BACKGROUND OF THE INVENTION

The present invention is to a new and distinct variety of mandarin clementine tree, which is named 'AECO1'. 'AECO1' is a mandarin clementine selection developed in Valencia, Spain, from an irradiated bud of the unpatented *Citrus clementina* 'Clemenules', which is a mutation of the unpatented *Citrus clementina* 'Clementina Fina' originating in Nules, Castellon, Spain.

'AECO1' originated as a single plant and was asexually reproduced by grafting budwood onto 'Troyer' (unpatented) rootstocks. 'AECO1' was selected and propagated as follows: Irradiation of budwood from 'Clemenules' trees was developed by using 40 Grays on the surface on the plant material of gamma irradiation from Cobalt-60 irradiation source. Buds from this irradiation were propagated onto rootstocks in a greenhouse located in Pego, Alicante, Spain, where the plants were grown to a size appropriate for field planting. These trees were planted in 2016 in a controlled, confidential field at a farm in Pego, Spain. Fruit on the trees was evaluated during three fruit cycles and several trees producing fruit were identified. Additional propagation of 'AECO1' were maintained in the greenhouse at the farm in Pego, Spain.

SUMMARY OF THE INVENTION

The present invention provides a novel mandarin clementine variety having the characteristics described and illustrated herein. The variety, 'AECO1', is a mandarin clementine selection developed at a commercial farm in Alicante, Spain, from an irradiated bud of the unpatented mandarin cultivar 'Clemenules'. 'AECO1' combines the early season maturity, moderated sized flattened shape fruit, and a bright intense reddish orange skin color. It further distinguishes itself by being very low seeded and easy to peel, featuring a resistance to temperature abiotic stress, and for the further characteristics to be detailed herein.

COMPARISON TO PARENT VARIETY

Differences between 'AECO1' and the parent and similar variety 'CLEMENULES' are summarized below, as well as in Table 1.

1. Fruit time of maturity for consumption in 'AECO1' is earlier than 'Clemenules' and presence of navel opening is occasionally present in the former and absent in the latter.
2. Fruit main color of flesh in 'AECO1' is dark orange with a strong surface glossiness while 'Clemenules' shows a medium orange color and a weak surface glossiness.
3. 'AECO1' shows a significant high temperature resistance whereas 'Clemenules' resistance is moderate and there is no puffing on tree in 'AECO1''s fruit while puffing happens in 'Clemenules' fruit on tree.
4. Presence of areola in 'AECO1' is absent while in 'Clemenules' is incomplete, displaying the former a medium strength of segment walls when the latter exposes a strong strength of segment walls.

5. Concerning colors, the albedo in 'AECO1' is light whitish yellow, rind color is medium orange and adherence weak; in 'Clemenules', albedo is white and the rind color is pale orange with a strong rind adherence.
6. Pollen viability in 'AECO1' is absent with an average of less than one seed per fruit, contrasting 'Clemenules' high pollen viability high with an average of twenty to forty seeds per fruit.
7. 'AECO1' distinguishes itself by being very low seeded (<1 seed per fruit) differing from 'Clemenules' which will set as many as about 10 seeds in cross-pollinated situations.

TABLE 1

Comparison of 'AECO1' with 'Clemenules'

| Characteristic | 'AECO1' | 'CLEMENULES' |
|---|---|---|
| Anther color | white | yellow |
| Anther: pollen viability | absent | present |
| Pollen viability | low (<10% germination) | High |
| Fruit oil glands | Present, evenly sized | Absent |
| General rind color | Orange | Medium pale orange |
| Maturity | Early October | Mid October |
| Fruit: color of albedo | RHS Yellow-White 158A | RHS White 155A |
| Fruit: rind adherence | Weak | Strong |
| Seeds/fruit | Average less than 1 | 20-40 |
| Leaf blade: shape in cross section | Straight or weakly concave | Intermediate |
| Fruit: position of broadest part: | Towards distal end | At middle |
| Fruit: presence of areola | Absent | Incomplete |
| Fruit: presence of navel opening | Occasionally present | Absent |
| Fruit surface: glossiness (shininess) | Strong | Weak |
| Fruit: general main color of flesh | Dark orange | Medium orange |
| Fruit: strength of segment walls | Medium | Strong |
| Time of maturity of fruit for consumption | Early to mid-season | Mid-season |
| Resistant to high temperatures | High | Moderate |
| Puffing | Not puffing | Puffing |

BRIEF DESCRIPTION OF THE PHOTOGRAPHS

The accompanying photographic illustration shows typical samples of vegetative growth of 4-year old specimens of the new variety, in color as nearly true as it is reasonably possible to make in a color illustration of this character. Plants were grown in Alicante, Spain. Colors in the photograph may differ from the color values cited in the detailed botanical description below, which accurately describes the colors of the new Clementine.

COMPARISON WITH KNOWN VARIETIES

Figure 1:
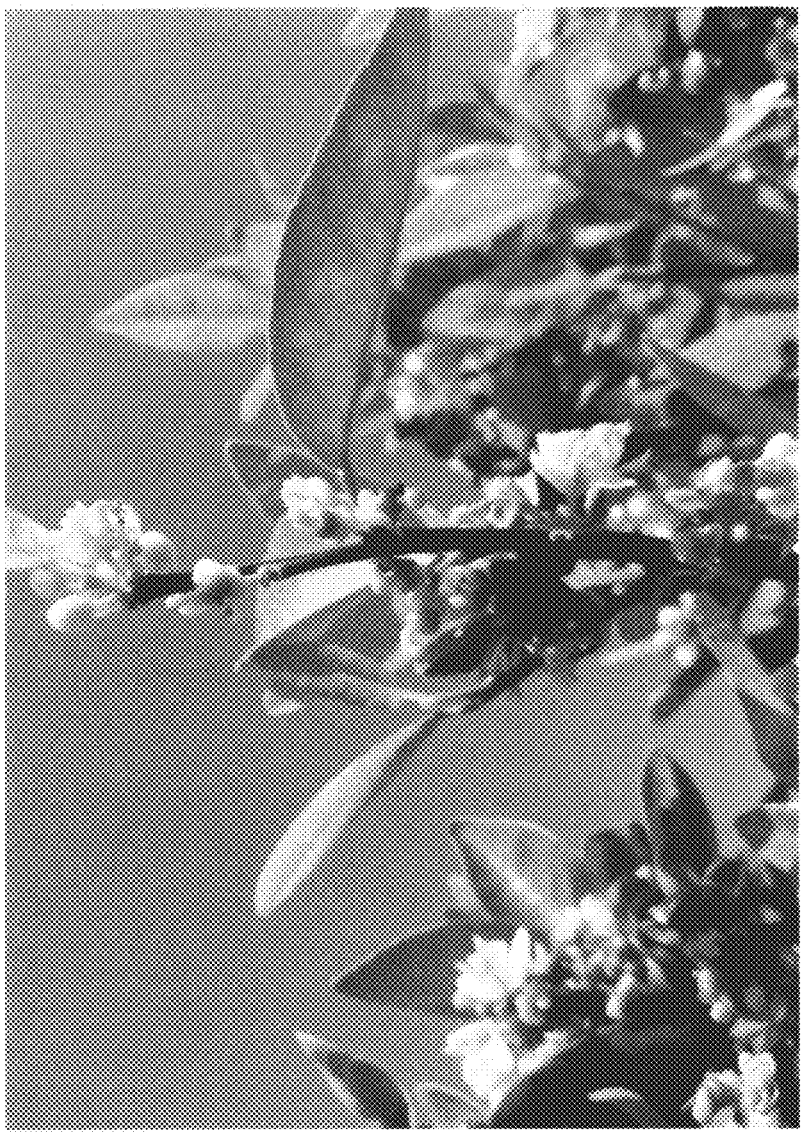
FIG. 1 illustrates flowers of 'AECO1'.
Figure 2:
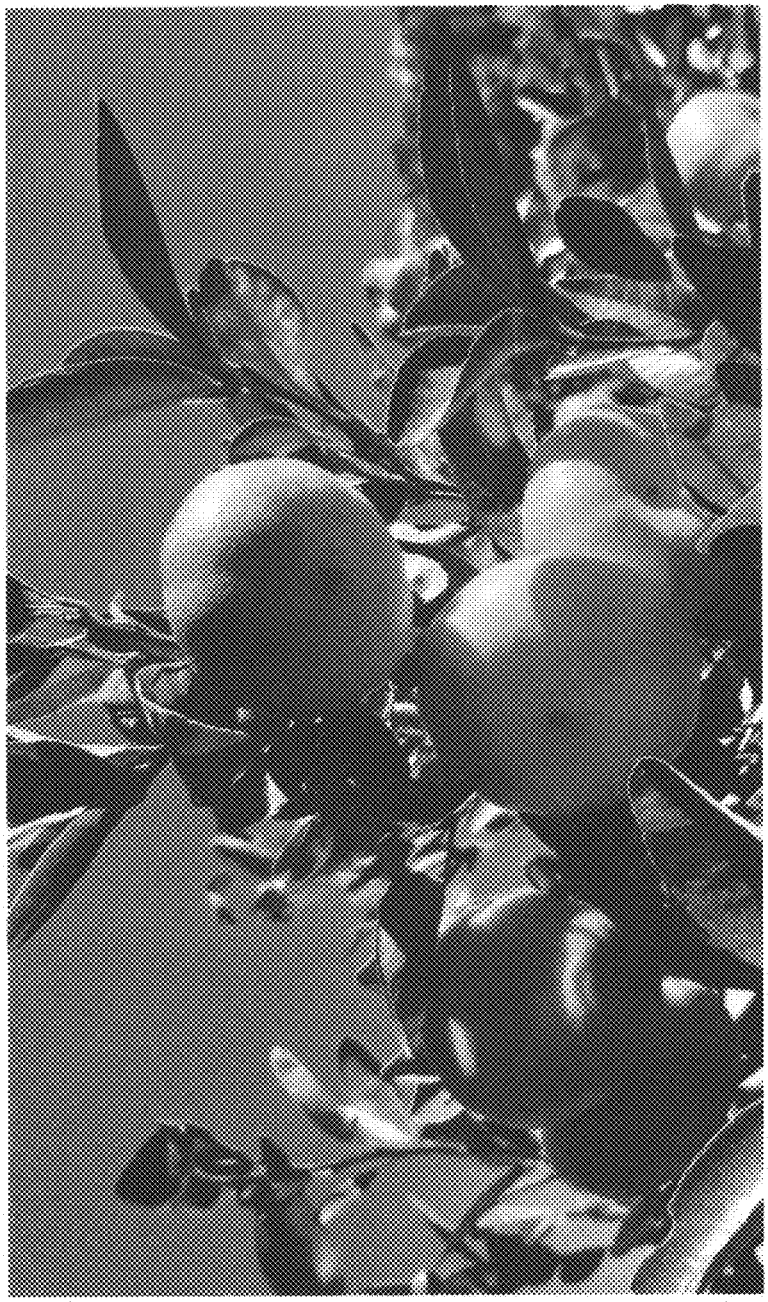
FIG. 2 illustrates fruits of 'AECO1'.
Figure 3:
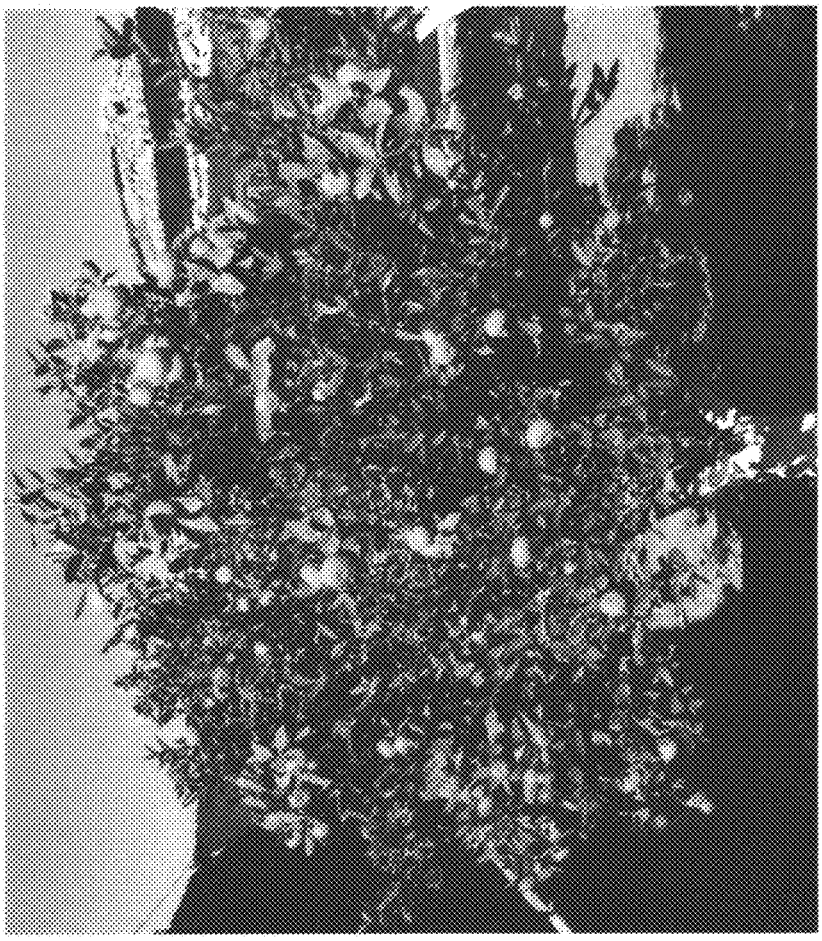
FIG. 3 illustrates a tree of 'AECO1'.
Figure 4:
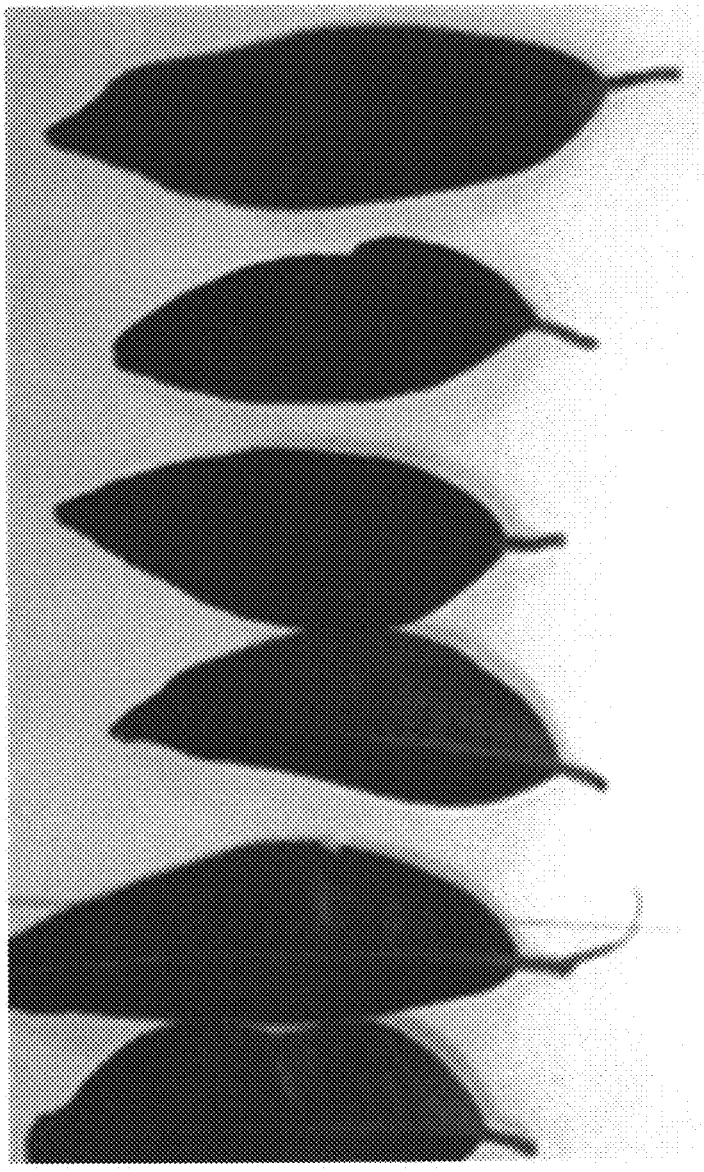
FIG. 4 illustrates foliage of 'AECO1'.

The new variety 'AECO1' can be compared to the unpatented commercial variety 'Marisol'. 'AECO1' differs from 'Marisol' in the following:

1. 'AECO1' has no viable pollen, 'Marisol' has a moderate amount of viable pollen.
2. Fruit rind color of 'AECO1' is darker than fruit rind color of 'Marisol'.

The new variety 'AECO1' can be compared to the unpatented commercial variety 'Arrufatina'. 'AECO1' differs from 'Arrufatina' in the following:

1. 'AECO1' has no viable pollen, 'Arrufatina' has a moderate amount of viable pollen.
2. Fruit rind color of 'AECO1' is much darker than fruit rind color of 'Arrufatina'.
3. Fruit maturity of 'AECO1' begins approximately 2 weeks earlier than 'Arrufatina'.

The new variety 'AECO1' can be compared to the commercial variety 'Clemenpons' (U.S. Patent Application Publication No. 2003/0135903 P1, abandoned). 'AECO1' differs from 'Clemenpons' in the following:

1. 'AECO1' has no viable pollen, 'Clemenpons' has an abundant amount of viable pollen.
2. Fruit rind color of 'AECO1' is darker than fruit rind color of 'Clemenpons'.
3. Fruit maturity of 'AECO1' begins approximately 2 weeks earlier than 'Clemenpons'.
4. Rind adherence is weak in the new variety; rind adherence is strong in this comparator.
5. The new variety 'AECO1' is not susceptible to "puffing", as is 'Clemenpons'. "Puffing" is defined as a condition where fruit segments become loosened from the interior skin surface and the fruit in its entirety becomes soft in feel and appearance.

DETAILED DESCRIPTION OF THE INVENTION

Evaluation of 'AECO1' began on the original tree at the farm in Alicante, Spain 2016. Tree size, growth and fruit production characteristics and fruit quality characteristics have been compared to 'Clemenules' from the same location. 'AECO1' trees have also been evaluated for three years at the same location.

The tree size and growth characteristics of 'AECO1' have been consistent with 'Clemenules' throughout the whole evaluation. The tree height reached an average of 2 meters high with a 2.5 meter dense crown diameter, displaying a moderately vigorous aspect. An upright trunk with a circumference of 35 cm and a smooth surface texture, covered by a brown bark (RHS N199A). Thorniness is absent. Tree growth habit is upright with production commencing in the second year after planting. Alternate bearing does not appear to be a problem of any significance while evidencing resistance to abiotic stress.

The branching arrangement is alternate with an amount from 2 to 7 lateral branches at an angle from main trunk of 115° C. to 140° C. Foliage displays a straight or weakly concave shape with an acute apex, and a medium mature leaf blade length of 8.5 cm and 3.5 cm width, showing an upper green leaf color (RHS 137A) and a green under leaf color (RHS 143A). A short petiole length of 0.8 millimeters, a width of 0.4 mm in a green color (RHS 143A) and smooth texture.

Fruit size is similar to 'Clemenules', approximately 58 mm diameter, 38 mm in height, averaging approximately 80 grams per fruit. Fruit is flattened in shape with a bright intense reddish orange rind color (RHS 28A) and a smooth rind texture, with an occasional navel presence and a hollow axis structure. Rind adherence and separation is weak, thickness is approximately 3 mm and the albedo is light whitish yellow (RHS 158A) with a 2 mm loose thickness.

Fruit flesh (pulp) color is dark orange (RHS 25A) and finely textured. There is an absence of fruit neck and style, showing oil glands with roughly all more or less the same size. Fruit weight averages 80 g and the inflorescence is absent. (See Summarized fruit characteristics in Table 3).

Fruit number of seeds (controlled manual self-pollination) is absent or very few, the number of seeds/fruit (cross-pollinated conditions) is of <1 on average. The seeds are "mono-embryonic" (there is absence of polyembryony). Regarding color palette of seeds: the external coat is yellowish white RHS 157A, the cotyledon yellowish green (RHS 145C), the inner coat color is a medium brown (RHS N199C), weight averages 2 grams per seed, with a length of 1.5 cm and a width of 0.7 cm and a core diameter of 0.5 cm. 'AECO1' distinguishes itself by being very low seeded (<1 seed per fruit) in all situations of cross-pollination.

Flowering habit is once per year, showing a complete flower structure and a size of 1.2 cm approx. Petal and anther colors are white (RHS 155B White) presenting an absence in pollen viability. Peduncles are strong and ribbed, with a length of 0.5 cm and diameter of 0.4 cm, at an approximate 40° to the lateral branch angle. Peduncle color is Green (RHS 140D) and calyx shapes displays a slightly rounded shape.

Fruit is juicy, with a rich sweet flavor when mature. The fruit is relatively easy to peel with 136% soluble solids (at maturity) a high percentage of juice (55%) and a medium acidity at maturity. Fruit quality after storage is excellent, approximately 30 days at 5° C.

In Pego, Alicante 'AECO1', fruit matures from October until late December. 'AECO1' holds its fruit quality characteristics in tree 75 days past maturity. The temperature ranges at the Pego Farm oscillates from 40° C. to 0° C. during the day and from 25° C. to 0° C. at nighttime. The tree of the new variety 'AECO1' evidenced a major resistance to extreme temperature of over 40° being also more efficient under average normal temperature.

The general soil condition at the farm in Pego is clay loamy. The trees of the new variety 'AECO1' displayed a resistance to abiotic stress beyond 'Clemenules' trees, evidencing a major resistance in the same soil conditions.

All major color code designations are made with reference to The Royal Horticultural Society Color Chart designations. The chart used in the identification of colors is The R.H.S. Colour Chart of The ROYAL HORTICULTURAL SOCIETY, 2015 edition, except where general colors of ordinary significance are used. Color values were taken under daylight conditions in full sunlight.

The Royal Horticultural Society (R.H.S.) color numbering system is used herein for the color description of the rind, seed bark, leaf, flower, flesh color and other interest of the 'AECO1' tree.

DETAILED BOTANICAL DESCRIPTION

Botanical classification: *Citrus clementina* 'AECO1'.

TABLE 2

Tree, leaf, and seed characteristics 'AECO1' for 4-year-old tree.

| | |
|---|---|
| Tree height | 2 m |
| Crown Density: | Dense |
| Crown diameter | 2.50 m |

TABLE 2-continued

Tree, leaf, and seed characteristics 'AECO1' for 4-year-old tree.

| | |
|---|---|
| Crown shape | Globular |
| Quantity of Lateral Branches | 2 to 7 |
| Branching Angle of Lateral Branches from Main Trunk: | 115° to 140° |
| Arrangement: | Alternate |
| Trunk circumference | 35 cm |
| Trunk surface texture | Smooth |
| Rootstock-scion compatibility | No incompatibility known |
| Tree vigor | Moderately vigorous |
| Bark color | RHS N199A Grey-Brown |
| Leaf arrangement | Asymmetric |
| Leaf aspect | Straight or weakly concave |
| Leaf Margin | Entire, or irregular, shallow, infrequent crenations |
| Leaf shape | Narrow ovate |
| Leaf blade length | 8.5 cm medium |
| Leaf blade width | 3.5 cm medium |
| Leaf apex | Acute |
| Mature Leaf upper color | RHS 137A Green |
| Mature Leaf under color | RHS 143A Green |
| Petiole length | 0.8 mm |
| Petiole width | 0.4 mm |
| Petiole color | RHS 143A Green |
| Petiole Texture: | Smooth |
| Petiole Wings | Absent |
| Thorniness | Absent |
| Inflorescence type | Single occurring flowers. |
| Flowering habit | Flowers once per year, Flowering occurs between February 20 until May 5 in Pego, Alicante. |
| Flower size | 1.2 cm |
| Flower fragrance: | Moderate |
| Calyx size: | 57 mm |
| Calyx shape: | Slightly rounded |
| Calyx color: | RHS 149C Yellow-Green |
| Calyx texture: | Slightly rough |
| Flower structure | Complete |
| Petal color | RHS 155B White |
| Petal Quantity: | 4 |
| Petal arrangement: | Symmetrical, not overlapping |
| Length: | 0.92 cm |
| Width: | 0.45 cm |
| Stamen length: | 57 mm |
| Anther color | RHS 155B White |
| Pollen viability | Non-viable |
| Pistil length: | 57 mm |

TABLE 3

Fruit characteristics of 'AECO1'
Averages

| | |
|---|---|
| Fruit shape | Flattened sphere |
| Fruit diameter | 58 mm |
| Fruit height | 38 mm |
| Fruit weight | 80 gr |
| Fruit: shape of distal end | Flattened |
| Fruit neck | Absent |
| Style | Non-persistent. |
| Rind texture | Smooth |
| Oil glands | Present, consistently sized |
| Fruit: color of flesh | RHS 25A Orange |
| Fruit: main color of skin | RHS 28A Orange. |
| Fruit areola | Not present |
| Rind thickness | 3 mm, medium |
| Albedo thickness | 2 mm, loose |
| Albedo color | RHS 158A Yellow-White |
| Albedo quantity adhering to flesh | Absent or very small |
| Albedo strands | Very small |
| Rind adherence | Weak |
| Rind separation | Weak |
| Flesh (pulp) texture | Medium |
| Number of segments | 11-13 |

TABLE 3-continued

| Fruit characteristics of 'AECO1' Averages | |
|---|---|
| Rudimentary segments | Absent, or very rare |
| Fruit juice vesicle size | Medium |
| Axis: structure | Hollow |
| Navel presence | Occasionally present |
| Fruit: number of seeds (controlled manual self-pollination) | Absent or few |
| Quantity of seeds/fruit(cross-pollinated conditions) | <1 on average |
| Seed: polyembryony | Absent (Mono embryonic) |
| Seed external coat | RHS 157A Green-White |
| Seed cotyledon color | RHS 145C Yellow-Green |
| Seed inner coat color | RHS N199C Grey-Brown |
| Seed weight | 2 grams |
| Seed length | 1.5 cm |
| Seed width | 0.7 cm |
| Seed core diameter | 0.5 cm |
| Juice % | High. 55% |

TABLE 3-continued

| Fruit characteristics of 'AECO1' Averages | |
|---|---|
| Soluble solids (at maturity) | 136% Medium |
| Acid (at maturity) | Medium |
| Season of maturity | Early (October-late December) |
| Productivity | 80 to 150 kilos per tree |
| Fruit holding ability on tree past maturity | 75 days |
| Shipping quality | Very good |
| Fruit quality after storage | Excellent (5° C., 30 days) |
| Market use | Fresh fruit |

What is claimed is:

1. A new and distinct cultivar of *Citrus* tree named 'AECO1' as herein illustrated and described.

* * * * *